United States Patent [19]

Iida et al.

[11] 4,370,419
[45] Jan. 25, 1983

[54] TRAY FOR IDENTIFYING MICROORGANISMS

[75] Inventors: Tamotsu Iida, Oyama; Seiji Enomoto, Saitama; Michiya Kimura, Oyama, all of Japan

[73] Assignee: Eiken Chemical Co., Ltd., Tokyo, Japan

[21] Appl. No.: 283,473

[22] Filed: Jul. 15, 1981

[30] Foreign Application Priority Data

Mar. 18, 1981 [JP] Japan ............................ 56-38022[U]

[51] Int. Cl.³ ............................................. C12M 1/20
[52] U.S. Cl. .................................. 435/301; 435/808; 422/57; 422/61
[58] Field of Search ................................ 435/299–301, 435/293, 294, 808; 422/57, 62, 61

[56] References Cited

U.S. PATENT DOCUMENTS 4,076,592  2/1978  Bradley ............................ 435/301
4,239,853  12/1980  Bradley ............................ 435/301
4,292,273  9/1981  Butz et al. ........................ 435/301

Primary Examiner—Benoît Castel
Attorney, Agent, or Firm—Stevens, Davis, Miller & Mosher

[57] ABSTRACT

A tray for identifying isolated microorganisms, comprising a plastic or glass tray body and a cover, the body surface of which has two kinds of hollow cells for bacterial suspension. One is formed horizontally across the surface of the tray and the other is composed of a number of long and slender, parallel small cells. Each of the small cells communicates over a crest barrier with another hollow cell. Each crest barrier is formed so that its top is lower in height than the upper surface of the partition wall of the tray body. With this tray, microorganisms can be exactly and easily identified by improving the accuracy of uniformly pouring bacterial suspension into respective cells for bacterial suspension.

3 Claims, 4 Drawing Figures

TRAY FOR IDENTIFYING MICROORGANISMS

BACKGROUND OF THE INVENTION

This invention relates to identifying microorganisms and, more particularly, to improvements in a tray containing trace amounts of reagents for identifying microorganisms.

The inventors of this invention have proposed a tray containing trace amounts of reagents for identifying microorganisms as disclosed in the pending U.S. patent application Ser. No. 171,819 filed on July 24, 1980, now abandoned and assigned to the same applicant as that of this application, a continuation of which was filed on Oct. 29, 1981. In this tray, the cells for bacterial suspension are continuously aligned adjacent to each other longitudinally of the tray body and perpendicularly to the cell for bacterial suspension. Accordingly, it is difficult to uniformly pour bacterial suspension into the respective cells for bacterial suspension, which cells communicate with the respective small cells, and it is also difficult to secure specified quantity of bacterial suspension in the respective cells for bacterial suspension. Further, since the crest barriers for communicating the cells for bacterial suspension with the respective small cells are formed with relatively low gradients raised at both sides of the crest, the bacterial suspension may sometimes counterflow from the small cells to the cells for bacterial suspension.

SUMMARY OF THE INVENTION

Accordingly, a primary object of this invention is to provide a tray for identifying microorganisms which can eliminate the aforementioned disadvantages and drawbacks of the conventional tray.

Another object of this invention is to provide a tray for identifying microorganisms which can improve the accuracy of uniformly pouring bacterial suspension into respective cells for bacterial suspension.

A further object of this invention is to provide a tray for identifying microorganisms which can exactly secure the retaining capacity of bacterial suspension uniformly poured into the respective cells for bacterial suspension.

Yet another object of this invention is to provide a tray for identifying microorganisms which can completely prevent bacterial suspension to be tested from counterflowing from the small cells to the respective cells for bacterial suspension.

Still another object of this invention is to provide a tray for identifying microorganisms which can improve the stability of media ingredients and the drying potency of reagents placed in the small cells.

BRIEF DESCRIPTION OF THE DRAWINGS

The above and other related objects and features of the invention will be apparent from a reading of the following description of the disclosure found in the accompanying drawings and the novelty thereof pointed out in the appended claims.

DESCRIPTION OF THE PREFERRED EMBODIMENTS

Figure 1:
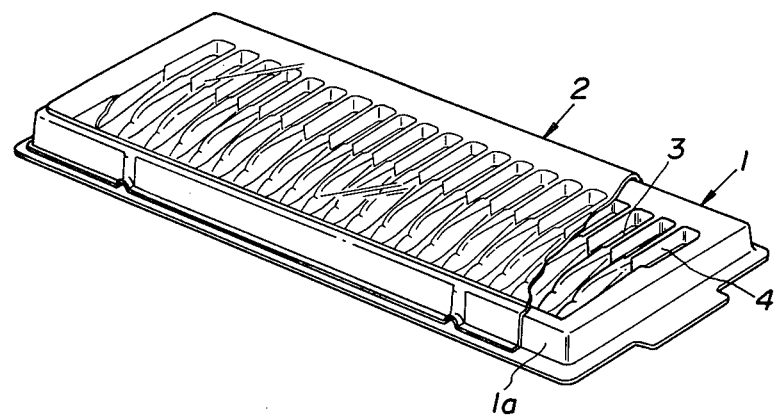
FIG. 1 is a perspective view of one preferred embodiment of the tray partly broken at the cover, constructed according to this invention.
Figure 2:
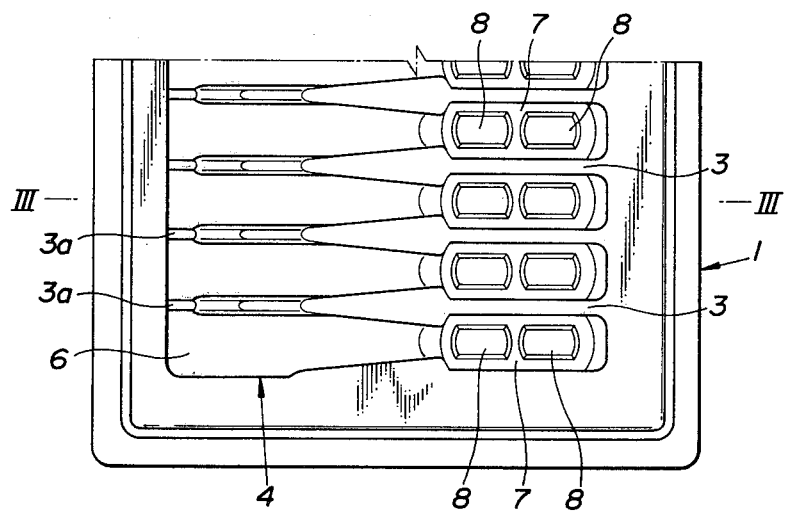
FIG. 2 is a partially enlarged plan view of the tray body shown in FIG. 1.

Referring now to the drawings, and particularly to FIGS. 1 and 2, the tray of this invention comprises a rectangular, thin, box-shaped tray body 1 and a cover 2. In the tray body 1, there are formed a number of cells 4 divided by a number of partition walls 3 aligned longitudinally of the tray body 1 at substantially equal interval and perpendicularly to the cells 4. Each of the cells 4 is divided into a cell 6 for bacterial suspension and a small cell 7 through a crest barrier 5 formed substantially at the center of the cell 4.

Figure 3:
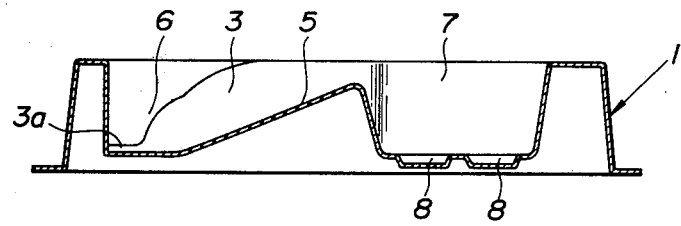
FIG. 3 is a sectional view of the tray body taken along the line III—III in FIG. 2.

As shown in FIG. 3, each of the crest barrier 5 is formed so that its top is lower in height than the upper surface of the partition wall 3 and has a gradual slope portion rising from the cell 6 for bacterial suspension and a steep slope portion downwardly lowered substantially vertically at the side of the small cell 7.

The partition wall 3 is substantially equal in height to the peripheral wall 1a of the tray body 1 except at the end near the cell 6 for bacterial suspension. The partition wall 3 is formed lower at end wall portion 3a, which is 2 mm in both width and height, and is approximately slightly raised from the bottom of the cell 6 for bacterial suspension at the end of the cell 6 for bacterial suspension. This end wall 3a of the partition wall 3 does not cause any trouble when pouring the bacterial suspension into the respective cells 6 for bacterial suspension, but serves to exactly retain the capacity of the bacterial suspension poured into the respective cells 6 for bacterial suspension.

Further, two shallow recesses or wells 8 are formed on the bottom of each of the small cells 7. These wells are so constructed as to dispersively place media ingredients to be disposed in the small cells 7.

Figure 4:
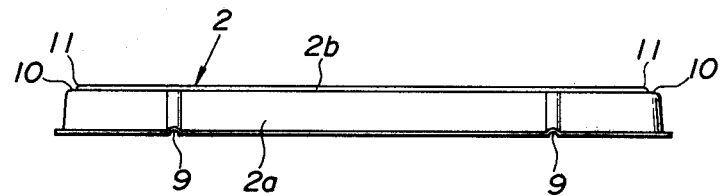
FIG. 4 is an enlarged side view of the cover of the tray body shown in FIG. 1.

As shown in FIG. 4, the cover 2 coating the tray body 1 is formed with a plurality of vent passages 9, four in the embodiment exemplified in FIGS. 1 through 4. These vent passages bulge outwardly in vertical direction at predetermined positions of the peripheral wall 2a to communicate the interior of the tray body 1 with the atmosphere and to accordingly communicate air between the small cells and the atmosphere at the time of culturing therein so as to thus accurately identify the microorganisms. Further, the cover 2 is also formed with a shoulder portion 10 bent slightly inwardly from the upper end of the peripheral wall 2a thereof, and is formed with the upper surface 2b on the upper end of the wall portion 11 rising upwardly from the shoulder portion 10. Thus, the interior of the tray body 1 is isolated from the upper surface 2b of the cover 2. In this manner, this configuration can prevent the splash of the bacterial suspension from being adhered onto the back surface of the upper surface 2b of the cover 2 at the time of pouring the bacterial suspension. There can also be engagement between the bottom of the tray body of upper side with the shoulder portion 10 of the cover 2 coated on the tray body 1 of lower side when a plurality of tray bodies 1 are stacked, thereby exactly stacking the tray bodies 1.

When this tray body 1 thus constructed is used, dried reagents are prepared beforehand in the wells of the respective small cells 7, and a specified quantity of bacterial suspension is poured into each of the cells 6 for bacterial suspension. The tray body 1 is retained horizontally to level the bacterial suspension uniformly in the cells 6 for bacterial suspension. The entire tray body 1 is then inclined so that the cells for bacterial suspension becomes higher than the small cells. The bacterial suspension is thereby introduced into the respective small cells over the crest barriers, and is simultaneously inoculated therein. When the reagents are, if they are deteriorated upon mixture thereof with each other, separably placed in the respective ingredients in the respective wells, their stability can be retained.

It is noted that the cover 2 may be placed on the tray body 1 after pouring the bacterial suspension or may be put on the tray body 1 after inoculating it. Then, the bacteria inoculated is cultured by the conventional process to thereby react according to the type of the biochemical characteristics and the color change is to be observed. Thus, this tray body 1 can exactly identify the biochemical properties of the bacteria without erroneous operation in short time.

It should be understood from the foregoing description that the tray for identifying microorganisms of this invention thus comprises a tray body made of plastic or glass and a cover. The tray body has a number of cells divided by a number of partition walls aligned longitudinally of the tray body at substantially equal interval and perpendicularly to the cells. Each of the cells is divided into a cell for bacterial suspension and a small cell through a crest barrier formed substantially at the center of the cell. Each crest barrier is formed at its top to be lower in height than the upper surface of the partition wall and has a gradual slope portion rising from the cell for bacterial suspension and a steep slope portion downwardly lowered substantially vertically at the side of the small cell. Two wells are formed in each of the small cells, and the cells for bacterial suspension are communicated with the respective small cells over the crest barriers. The accuracy of uniformly pouring the bacterial suspension at the time of pouring the bacterial suspension into the respective cells for bacterial suspension can thus be improved and the retaining capacity of the bacterial suspension uniformly poured into the respective cells for bacterial suspension can be exactly secured by dividing the cells for bacterial suspension through the partition walls. The counterflow of the bacterial suspension to be tested from the small cells to the respective cells for bacterial suspension can be completely prevented by forming the crest barriers in the shape as was described before, and the reagents to be used for culture and test can be dispersively disposed in two or more wells in the respective small cells, thereby improving the drying efficacy of the reagents at the time of producing the same, or increasing the stability of the media ingredients by separately placing respective ingredients which tend to be deteriorated upon mixture thereof in the media ingredients in the respective wells.

What is claimed is:

1. A tray for identifying microorganisms, comprising: a tray body, comprising:
   a first wall which defines an interior space;
   a plurality of parallel cells extending across said interior space;
   a plurality of parallel partition walls separating said cells and extending across said interior space, having a height substantially equal to that of said first wall;
   a plurality of crest barriers extending substantially perpendicularly across substantially the middles of said cells between pairs of said partition walls and dividing each of said cells into a flat bottomed cell for bacterial suspension and a small cell, each of said crest barriers having a gradual slope portion rising from one of said cells for bacterial suspension and a steep slope portion rising substantially vertically from one of said small cells, said crest barriers each having a height less than that of said partition walls, each of said partition walls having a reduced height portion abutting said first wall adjacent a pair of said cells for bacterial suspension, each of said small cells being wider than said crest barriers and having a bottom with at least two wells, each of said crest barriers decreasing in width from said cell for bacterial suspension to said small cell; and
   a cover fitting over said tray body comprising:
   a top;
   a peripheral wall; and
   a lower lip, said peripheral wall and said lower lip being provided with a plurality of outwardly bulging vent passages to allow communication of the interior space of said tray body with the atmosphere.

2. The tray according to claim 1, wherein said cover is formed with a shoulder portion bent slightly inwardly from the upper end of the peripheral wall of said tray body and is formed with the upper surface on the upper end of the wall portion rising upwardly from the shoulder portion of said cover.

3. The tray according to claim 1, wherein each of said partition wall reduced height portions is about 2 mm high and 2 mm wide.

* * * * *